(12) United States Patent
Kwak et al.

(10) Patent No.: US 10,111,802 B2
(45) Date of Patent: Oct. 30, 2018

(54) WEARABLE ROBOT AND METHOD OF CONTROLLING THE SAME

(71) Applicant: Samsung Electronics Co., Ltd., Suwon-Si, Gyeonggi-Do (KR)

(72) Inventors: No San Kwak, Suwon-si (KR); Young Bo Shim, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 948 days.

(21) Appl. No.: 14/558,029

(22) Filed: Dec. 2, 2014

(65) Prior Publication Data

US 2015/0164731 A1    Jun. 18, 2015

(30) Foreign Application Priority Data

Dec. 16, 2013   (KR) .................. 10-2013-0156410

(51) Int. Cl.
    *A61H 3/00*    (2006.01)
    *A61F 2/72*    (2006.01)
    *A61H 1/02*    (2006.01)

(52) U.S. Cl.
CPC ............... *A61H 3/00* (2013.01); *A61F 2/72* (2013.01); *A61H 1/024* (2013.01); *A61H 1/0244* (2013.01); *A61H 1/0266* (2013.01); *A61H 2201/1215* (2013.01); *A61H 2201/1246* (2013.01); *A61H 2201/164* (2013.01); *A61H 2201/165* (2013.01); *A61H 2201/1628* (2013.01); *A61H 2201/1676* (2013.01); *A61H 2201/5007* (2013.01); *A61H 2201/5035* (2013.01); *A61H 2201/5038* (2013.01); *A61H 2201/5061* (2013.01); *A61H 2201/5069* (2013.01); *A61H 2203/0406* (2013.01); *A61H 2205/088* (2013.01); *A61H 2205/10* (2013.01); *A61H 2205/12* (2013.01);

(Continued)

(58) Field of Classification Search
CPC ........ A61H 3/00; A61H 1/024; A61H 1/0244; A61H 1/0266; A61H 2201/1215; A61H 2201/1246; A61H 2230/105; A61H 2230/045; A61H 2205/12; A61H 2205/10; A61H 2205/088; A61H 2201/5069; A61H 2201/5035; A61H 2201/5007; A61H 2201/1676; A61H 2201/165; A61H 2201/164; A61H 2201/1628; A61H 2201/5061; A61F 2/72

See application file for complete search history.

(56) References Cited

U.S. PATENT DOCUMENTS

2002/0171680 A1   11/2002  Beranek et al.
2006/0211956 A1*   9/2006  Sankai ............... A61B 5/04888
                                                               601/5

(Continued)

FOREIGN PATENT DOCUMENTS

| JP | 2007202882 A | 8/2007 |
|----|---|---|
| KR | 1020100026207 A | 3/2010 |
| KR | 1020130039546 A | 4/2013 |

*Primary Examiner* — Quang D Thanh
(74) *Attorney, Agent, or Firm* — Harness, Dickey & Pierce, P.L.C.

(57) ABSTRACT

There is provided a method of controlling a wearable robot. The method includes measuring an electrical signal from a scalp of a wearer, estimating a current walking speed of the wearer using the measured electrical signal, and outputting assistive torque which allows the estimated current walking speed to approximate a target walking speed.

18 Claims, 8 Drawing Sheets

(52) U.S. Cl.
CPC .. *A61H 2230/045* (2013.01); *A61H 2230/105* (2013.01)

(56) References Cited

U.S. PATENT DOCUMENTS

| | | | |
|---|---|---|---|
| 2008/0288020 A1* | 11/2008 | Einav | A61N 1/36003 607/48 |
| 2011/0105966 A1* | 5/2011 | Kazerooni | A61H 3/008 601/35 |
| 2012/0071797 A1* | 3/2012 | Aoki | A61H 1/024 601/34 |
| 2013/0096453 A1 | 4/2013 | Chung et al. | |
| 2013/0158445 A1* | 6/2013 | Kazerooni | A61H 3/00 601/35 |
| 2014/0277582 A1* | 9/2014 | Leuthardt | A61F 2/54 623/25 |
| 2015/0012111 A1* | 1/2015 | Contreras-Vidal | A61B 5/0476 623/25 |

* cited by examiner

WEARABLE ROBOT AND METHOD OF CONTROLLING THE SAME

CROSS-REFERENCE TO RELATED APPLICATION

This application claims the benefit of Korean Patent Application No. P2013-156410, filed on Dec. 16, 2013 in the Korean Intellectual Property Office, the entire disclosure of which is incorporated herein by reference.

BACKGROUND

1. Field

Example embodiments relate to a wearable robot and/or a method of controlling the same. For example, some example embodiments relate to a wearable robot for adjusting a walking speed and a method of controlling the same.

2. Description of the Related Art

Currently, there is development of wearable robots that have various purposes of, for example, aiding movement of the disabled or elderly by assisting with muscle strength while moving, rehabilitation therapy for patients of muscle diseases, assisting with heavy military gear worn by soldiers, and lifting of heavy loads in the field of industry.

In general, such wearable robots for supporting muscle strength may include an upper extremity assistant wearable robot for moving an upper extremity and a lower extremity assistant wearable robot for moving a lower extremity. Between the two wearable robots, the lower extremity assistant robot is a robot that is worn by a wearer on a lower half and reduces a muscle strength load of the wearer by applying assistive torque to a joint of, for example, a hip or a knee. The lower extremity wearable robot for assisting with the lower extremity muscle strength may assist with various motions in the wearer's daily life, such as walking along a flatland or a slope, going up and down stairs, and sitting down and standing up.

SUMMARY

Example embodiments relate to a wearable robot for generating and applying assistive torque in consideration of a current walking speed of a wearer that is estimated based on an electrical signal measured from a scalp of the wearer, and/or a method of controlling the same.

Some example embodiments relate to a method of controlling a wearable robot.

In some example embodiments, the method includes measuring an electrical signal from a scalp of a wearer, estimating a current walking speed of the wearer using the measured electrical signal, and outputting assistive torque which allows the estimated current walking speed to approximate a target walking speed.

Other example embodiments relate to a wearable robot.

In some example embodiments, the wearable robot includes an electrical signal measurement unit configured to measure an electrical signal from a scalp of a wearer, and a control unit configured to estimate a current walking speed of the wearer using the electrical signal measured through the electrical signal measurement unit and calculate assistive torque which allows the estimated current walking speed to approximate a target walking speed.

BRIEF DESCRIPTION OF THE DRAWINGS

These and/or other aspects of the example embodiments will become apparent and more readily appreciated from the following description of some of the example embodiments, taken in conjunction with the accompanying drawings of which.

DETAILED DESCRIPTION

Purposes, specific advantages, and novel features of the example embodiments will be apparent from the following detailed description in connection with the accompanying drawings. In this specification, when reference numerals are assigned to components of each drawing, it should be noted that, when the same components are illustrated in different drawings, the same numerals are assigned to the same components whenever possible. In the description, when detailed descriptions of related well-known technology are deemed to unnecessarily obscure the gist of the discussion, they will be omitted. In this specification, although the terms first, second, etc. are used to distinguish one component from another, these components are not limited by these terms.

In the drawings, the thicknesses of layers and regions are exaggerated for clarity. Like reference numerals in the drawings denote like elements.

Detailed illustrative embodiments are disclosed herein. However, specific structural and functional details disclosed herein are merely representative for purposes of describing example embodiments. Example embodiments may be embodied in many alternate forms and should not be construed as limited to only those set forth herein.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Hereinafter, a wearable robot and a method of controlling the same according to some example embodiments will be described in detail with reference to the accompanying drawings.

Example embodiments will be described with a robot for assisting with lower extremity muscle strength as an example among wearable robots. However, example embodiments do not apply specifically to only the robot for assisting with lower extremity muscle strength, but may apply to any wearable robot that assists with muscle strength of a wearer FIG. 1 is a diagram illustrating an appearance of a wearable robot according to some example embodiments.

Figure 1:
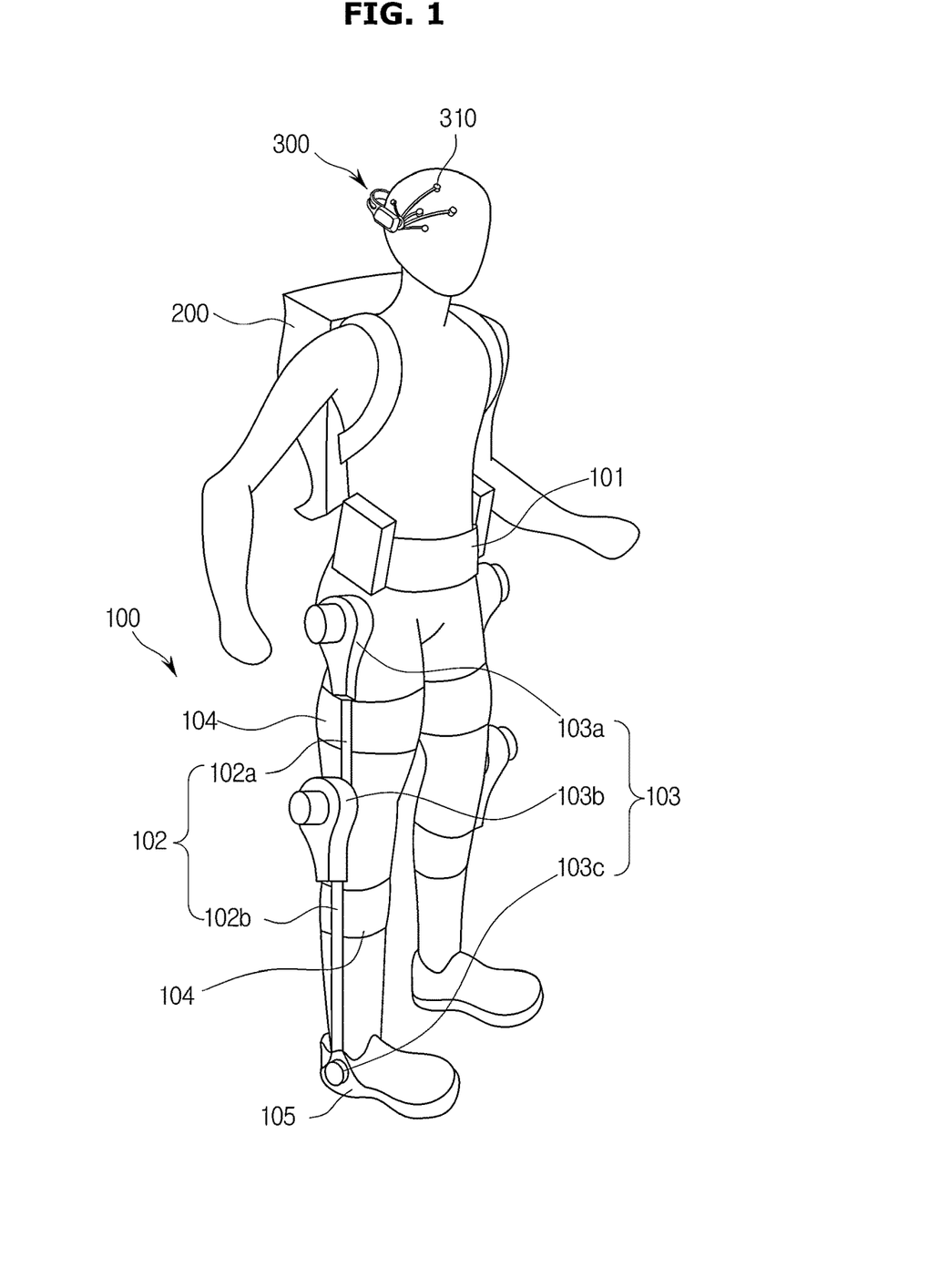
FIG. 1 is a diagram illustrating an appearance of a wearable robot according to some example embodiments.

As illustrated in FIG. 1, the wearable robot may include a mechanical unit 100, a control unit 200, and an electrical signal measurement unit 300.

The mechanical unit 100 is configured as a mechanism for assisting the wearer with walking, and may include components such as joints for a walking motion, actuators such as a motor and hydraulic and pneumatic cylinders, and a belt for attaching to a leg. This mechanical unit 100 may assist the wearer with the walking motion by operation of the joints and the actuators.

For example, as illustrated in FIG. 1, the mechanical unit 100 may include a waist wearing unit 101, a supporting unit 102, a joint unit 103, a fixing unit 104, and the like.

The waist wearing unit 101 may be worn around a waist of the wearer, and may be implemented so as to be modified according to a shape or a size of the waist of the wearer, but example embodiments are not limited thereto. Therefore, the waist wearing unit 101 may stably support a waist of a body according to a body shape of the wearer without modification.

Although not specifically illustrated in FIG. 1, the waist wearing unit 101 may include a waist support (not illustrated) for stably supporting the waist of the wearer and a band unit (not illustrated) that is formed to wrap around an abdominal portion of the wearer.

Since the waist wearing unit 101 made of the band unit (not illustrated) and the waist support (not illustrated) may wrap around an abdomen and a back of a waist of the wearer, the mechanical unit 100 may minimize a load burden applied to the waist of the wearer.

The supporting unit 102 supports walking of the wearer and may include a first support frame 102a and a second support frame 102b. The first support frame 102a and the second support frame 102b may have constant lengths, as illustrated in FIG. 1, however, example embodiments are not limited thereto. The first support frame 102a and the second support frame 102b may be formed in the form of bars having plate shapes, but example embodiments are not limited thereto.

The first support frame 102a may be positioned above a knee of the wearer, an end may be connected to the aforementioned waist wearing unit 101, and the other end may be connected to the second support frame 102b. In addition, the second support frame 102b may be positioned below the knee of the wearer, an end may be connected to the first support frame 102a and the other end may be connected to a shoe unit 105.

In this case, a part connecting the end of the first support frame 102a and the waist wearing unit 101, a part connecting the other end of the first support frame 102a and the end of the second support frame 102b, and a part connecting the other end of the second support frame 102b and the shoe unit 105 may be rotatably connected to each other, but example embodiments are not limited thereto.

Further, each connecting part may have at least one degree of freedom (DOF), but example embodiments are not limited thereto. Here, the term "DOF" refers to a DOF in forward kinematics or inverse kinematics. The DOFs of the mechanism refer to the number of variables that determine the number of independent movements of the mechanism or independent movement of a relative position between links. For example, an object in a 3D space formed by x, y, and z axes has at least one DOF among three DOFs (positions along each axis) for determining a spatial position of the object and three DOFs (rotation angles about each axis) for determining a spatial posture (orientation) of the object. Specifically, when the object can move along each axis and rotate about each axis, the object has may be understood as having six DOFs.

In addition, the first support frame 102a and the second support frame 102b may be adjusted to have lengths corresponding to a length of a leg of the wearer.

As illustrated in FIG. 1, a joint unit 103 may include a first joint 103a, a second joint 103b, and a third joint 103c, but example embodiments are not limited thereto.

The first joint 103a may be provided in the aforementioned part connecting the end of the first support frame 102a and the waist wearing unit 101, and facilitate bending between a hip and a thigh. The second joint 103b may be provided in the part connecting the other end of the first support frame 102a and the end of the second support frame 102b, and facilitate bending of the knee. The third joint 103c is provided in the part connecting the other end of the second support frame 102b and the shoe unit 105, and enables bending of an ankle.

As discussed below with reference to FIG. 2, a driving unit 110 may be provided in the first joint 103a, the second joint 103b, and the third joint 103c. The driving unit 110 may be configured to deliver driving force for rotation movement to the aforementioned first joint 103a, second joint 103b, and third joint 103c.

For example, the driving unit 110 may include a pair of gears (not illustrated) provided in each connecting part and a driving motor (not illustrated) that is connected to an axis of either gear of the pair of gears and is driven by receiving an electrical signal from the control unit 200, but example embodiments are not limited thereto. For example, instead of the driving motor (not illustrated), pneumatic and hydraulic methods may also be used.

Due to the driving force delivered from this driving unit 110, the first support frame 102a and the second support frame 102b may move with respect to the waist, the knee, and the ankle. Accordingly, the mechanical part 100 may bend the joints of the hip and the thigh, the knee, and the ankle.

Although not illustrated in FIG. 1, a joint angle measurement sensor for detecting a joint angle of each joint 103 may be further included. An encoder, a potentiometer, or the like may be used as the joint angle measurement sensor, but example embodiments are not limited thereto. In addition, specifically, the joint angle measurement sensor may be provided in the driving motor (not illustrated) of the driving unit 110.

A fixing unit 104 is a unit that fixes the first support frame 102a and the second support frame 102b on a lower extremity of the wearer, and may be implemented as a band, a belt, a clamp or the like, but example embodiments are not limited thereto. In this way, the first support frame 102a and the second support frame 102b are fixed above and below the knee, respectively, using the fixing unit 104. Therefore, the first support frame 102a and the second support frame 102b, which move, are able to stably assist the wearer with lower extremity muscle strength.

In addition, the mechanical unit 100 may further include the shoe unit 105. The shoe unit 105 may be configured to wrap around a foot of the wearer and determine a walking state of the wearer.

For example, as illustrated in FIG. 1, the shoe unit 105 may be configured to wrap around and protect the foot of the wearer, and measure the walking state of the wearer. As described above, a side surface of the shoe unit 105 may be rotatably connected to the other end of the second support frame 102b.

In addition, the driving motor (not illustrated) of the driving unit 110 for the second joint 103b is connected to the upper part of the shoe unit 105 combined with the second support frame 102b using a wire or the like. Therefore, the walk assistance robot may determine a bending angle of the ankle according to an angle changed by driving of the driving motor (not illustrated).

Also, although not illustrated in FIG. 1, a ground reaction force (GRF) measurement sensor may be provided in a bottom of the shoe unit 105. The GRF measurement sensor may be configured to measure GRF exerted on a bottom of the foot of the wearer from the ground. When gravity is exerted on the ground or internal force in a body is exerted on the ground, the GRF is a force exerted from the ground to the body that has the same magnitude as the gravity or the internal force and an opposite direction thereof. That is, the GRF may be understood as the force exerted by the wearer contacting on the ground.

In some example embodiments, a force sensing resistor (FSR), a pressure sensor, or the like may be used as the GRF measurement sensor, but example embodiments are not limited thereto.

In addition, in order to be easily and simply put on and taken off by the wearer, the shoe unit 105 may further include a fastening unit (not illustrated) such as a Velcro fastener or a snap fastener in the upper part to realize a one touch-type fixing structure.

In addition, the mechanical unit 100 may further include a power supply unit (not illustrated) for supplying power. In some example embodiments, the power supply unit may include a battery (not illustrated) so that the wearer can walk freely, but example embodiments are not limited thereto.

The electrical signal measurement unit 300 may be configured to measure an electrical signal from a scalp of the wearer and may include a plurality of electrodes 310 that are configured to attach to the scalp of the wearer as illustrated in FIG. 1.

Although not specifically illustrated in FIG. 1, the plurality of electrodes 310 may include a reference electrode, a ground electrode, and a measurement electrode for measuring the electrical signal. The number of measurement electrodes may be one or more, but example embodiments are not limited thereto.

In some example embodiments, a general electroencephalogram (EEG) apparatus may be used as the electrical signal measurement unit 300, but example embodiments are not limited thereto. The EEG apparatus may measure an EEG signal generated by electrical activity of a brain from the scalp in order to analyze brain activity. Further, the EEG apparatus may be configured to measure various types of electrical signals in addition to the EEG signal.

For example, the EEG apparatus may measures voltage fluctuations resulting from ionic current flows within neurons of the brain.

The electrical signal measured from the scalp using the electrical signal measurement unit 300 may include various types of electrical signals. The electrical signal may include, for example, an electrical signal generated by the electrical activity of the brain, an electrical signal generated by facial muscle movement, an electrical signal generated by head muscle movement resulting from a motion such as walking, and the like, but example embodiments are not limited thereto.

Hereinafter, for convenience of description, the electrical signal generated by the electrical activity of the brain is referred to as a first electrical signal, the electrical signal generated by the facial muscle movement is referred to as a second electrical signal, and the electrical signal generated by the head muscle movement resulting from walking is referred to as a third electrical signal.

In some example embodiments, the electrical signal measurement unit 300 is used to measure the third electrical signal related to walking among the aforementioned various types of electrical signals. That is, in some example embodiments, only the third electrical signal related to walking is used among the electrical signals from the scalp of the wearer measured using the electrical signal measurement unit 300. For example, in some example embodiments, the first and second electrical signals may be disregarded.

The electrical signal measured through the electrode 310 as described above has a minute value. Therefore, although not illustrated in the drawing, the electrical signal measurement unit 300 may further include a signal amplifying unit (not illustrated) configured to amplify the electrical signal measured through the electrode 310. The signal amplifying unit may amplify the electrical signal measured through the electrode 310 from one thousand times to one hundred thousand times.

The appearance of the wearable robot according to the embodiment has been described above. Hereinafter, each configuration of the wearable robot will be described.

Figure 2:
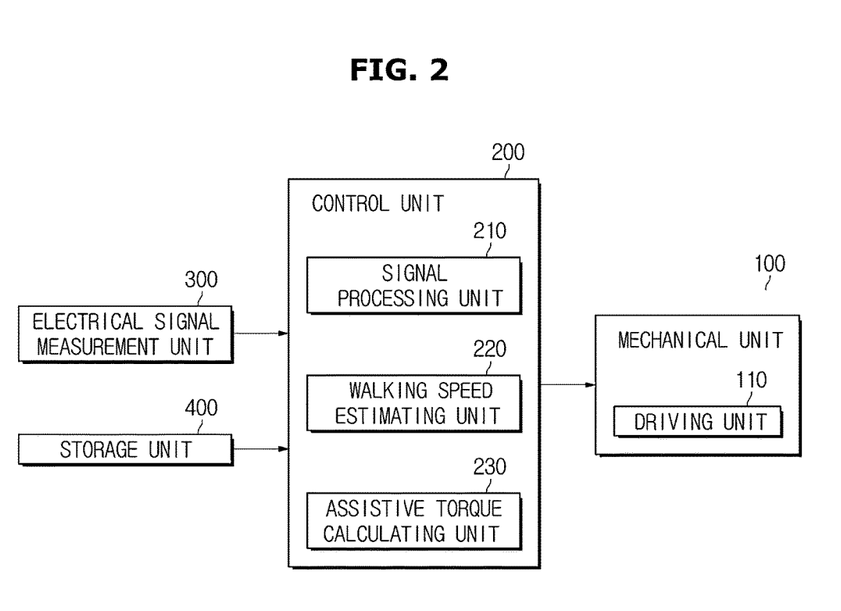
FIG. 2 is a block diagram illustrating a configuration of a wearable robot according to some example embodiments.

FIG. 2 is a block diagram illustrating a configuration of a wearable robot according to some example embodiments.

As illustrated in FIG. 2, the wearable robot may include a storage unit 400, the electrical signal measurement unit 300, the control unit 200, and/or the mechanical unit 100.

As described above, the electrical signal measurement unit 300 is configured to measure the electrical signal from the scalp of the wearer, and may include the plurality of electrodes 310 that are attached to the scalp of the wearer as illustrated in FIG. 1 and measure the electrical signal.

As discussed above, the aforementioned EEG apparatus may be used as the electrical signal measurement unit 300, but example embodiments are not limited thereto.

The electrical signal measurement unit 300 may measure all EEG signals generated by the electrical activity of the brain and the electrical signal generated by the facial muscle movement, the motion such as walking, and the like.

Typical EEG apparatus are utilized to analyze brain activity, therefore, the electrical signal generated by the facial muscle movement and the motion such as walking is often regarded as noise and is removed.

In contrast, in one or more example embodiments, the electrical signal measurement unit 300 and control unit 200 estimate a walking speed of the wearer by extracting the electrical signal associated with the motion of walking. For example, as described below, a signal processing unit 210 of the control unit 200 may be utilized to estimate the walking speed.

Also, although not illustrated in FIG. 2, since the electrical signal measured from the scalp has a minute value in units of microvolts μV in general, the electrical signal measurement unit 300 may further include a signal amplifying unit (not illustrated) configured to amplify the electrical signal measured using the electrode 310. This signal amplifying unit (not illustrated) is able to amplify the electrical signal measured using the electrode 310 from one thousand times to one hundred thousand times. In some example embodiments, the signal amplifying unit (not illustrated) may be provided in the control unit 200 rather than the electrical signal measurement unit 300.

The control unit 200 is configured to control overall operations of the wearable robot according to this embodiment.

In this embodiment, the control unit 200 may estimate a current walking speed of the wearer using the electrical signal measured using the aforementioned electrical signal measurement unit 300, calculate a difference value between the estimated current walking speed and a target walking speed, and calculate assistive torque for compensating the calculated difference value. In addition, the control unit 200 may generate a control signal for outputting the calculated assistive torque and transmit the generated control signal to the mechanical unit 100.

The control unit 200 may include a processor and a memory.

Figure 8:
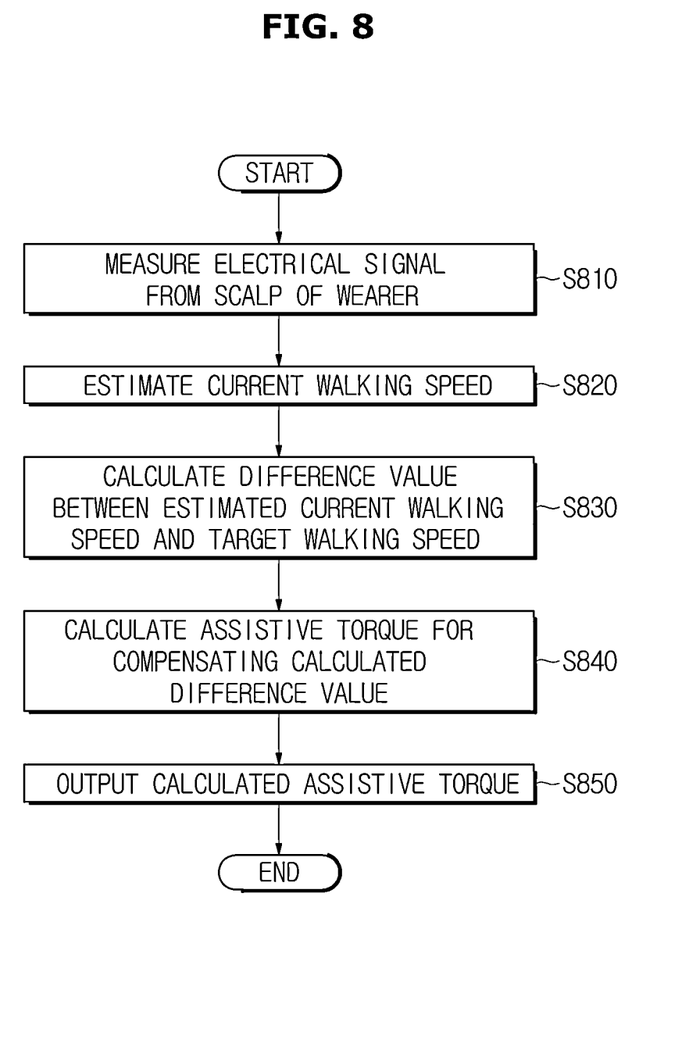
FIG. 8 is a flowchart sequentially illustrating a method of controlling a wearable robot according to some example embodiments.

The processor may be an arithmetic logic unit, a digital signal processor, a microcomputer, a field programmable array, a programmable logic unit, a microprocessor or any other device capable of responding to and executing instructions in a defined manner such that the processor is programmed with instructions that configure the control unit 200 as a special purpose computer to perform the operations illustrated in FIG. 8, such that the control unit 200 is configured to estimate a current walking speed of the wearer using measured electrical signals, calculate a difference value between the estimated current walking speed and a target walking speed, and calculate assistive torque to apply to the joints of the wearable robot to compensate for the calculated difference value. The measured electrical signals may be signals associated with head muscle movement extracted from a plurality of electrical signals generated by sensors 300 attached to a scalp of the wearer. The control unit 200 may be programmed with instructions that configure the control unit 200 to generate a control signal to the mechanical unit 100 to instruct the mechanical unit 100 to deliver driving force for rotation movement to the joints 103.

As illustrated in FIG. 2, the control unit 200 may include the signal processing unit 210, a walking speed estimating unit 220, and an assistive torque calculating unit 230, but example embodiments are not limited thereto.

For example, the processor of the control unit 200 may execute instructions that configure the control unit 200 as the signal processing unit 210, the walking speed estimating unit 220, and the assistive torque calculating unit 230.

The signal processing unit 210 may extract the third electrical signal generated by walking among the electrical signals measured using the electrical signal measurement unit 300.

As described above, the electrical signals measured using the electrical signal measurement unit 300 may include the first electrical signal generated by the electrical activity of the brain, the second electrical signal generated by the facial muscle movement, the third electrical signal generated by the head muscle movement upon walking, and the like.

In some example embodiments, the signal processing unit 210 may extract only the third electrical signal generated by the head muscle movement upon walking among the electrical signals measured by the electrical signal measurement unit 300.

Each of the first through third electrical signals may have an associated voltage that falls within a voltage band. Therefore, in some example embodiments, the electrical signals may be extracted by comparing a voltage level of each electrical signal with the voltage bands may be used, however, example embodiments are not limited thereto.

For example, the electrical signal generated by the electrical activity of the brain may have a value of 100 μV or less, the electrical signal generated by the facial muscle movement may have a value of 10 mV or less, and the electrical signal generated by the head muscle movement upon walking may have a value of 500 μV or less. In such a case, the signal processing unit 210 may extract only electrical signals having a value in the range of 100 μV to 500 μV from among the electrical signals measured using the electrical signal measurement unit 300.

The third electrical signal may be represented as a regular waveform in proportion to a walking cycle. However, the third electrical signal may also include an irregular waveform generated by various events occurring while walking. These events may include a head movement such as turning of the head and lowering of the head, speaking, a facial expression change, and the like, but example embodiments are not limited thereto. In this case, a filter for removing the irregular waveform as described above is additionally applied and only the waveform regularly generated in association with walking may be extracted from the third electrical signal.

The walking speed estimating unit 220 may perform frequency analysis on the third electrical signal extracted using the aforementioned signal processing unit 210 and estimate the current walking speed of the wearer based on a frequency analysis result.

For example, the walking speed estimating unit 220 may analyze the extracted third electrical signal as a plurality of frequency bands, obtain a frequency strength in each frequency band, calculate an average frequency of the third electrical signal using the obtained frequency strength for each frequency band, and estimate the current walking speed of the wearer using the calculated average frequency.

The walking speed estimating unit 220 may utilize various methods to estimate the current walking speed of the wearer. For example, as discussed below, the walking speed estimating unit 220 may utilize one or more of the following two methods to estimate the current walking speed of the wearer based on the calculated average frequency, but example embodiments are not limited thereto.

A First Method of Estimating a Walking Speed

In the first method, the walking speed estimating unit 220 may store an average frequency for each walking speed that is obtained through a pre-experiment is stored in the form of a lookup table (LUT) in the storage unit 400. The walking speed estimating unit 220 may find a walking speed corresponding to the average frequency calculated as described above in the LUT stored in the storage unit 400.

For example, an method of obtaining an average frequency for each walking speed through an experiment will be described as follows.

Figure 3:
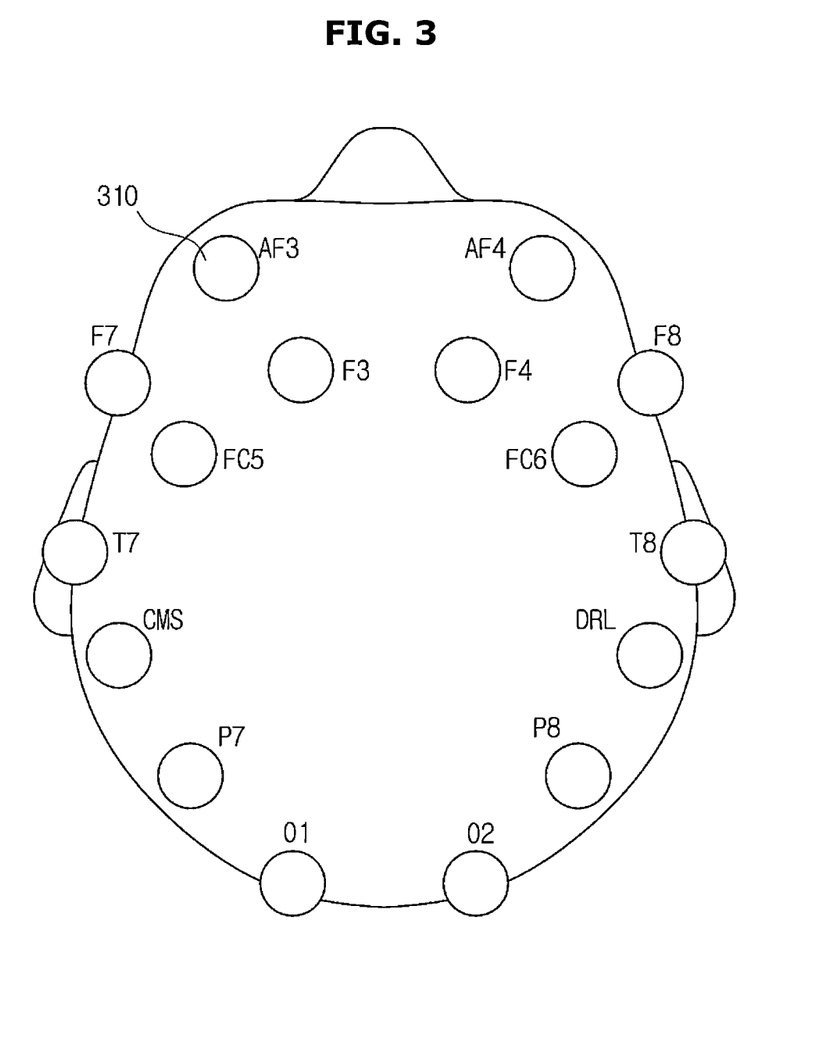
FIG. 3 is a diagram illustrating positions of electrodes arranged on a head of a wearer according to some example embodiments.

FIG. 3 is a diagram illustrating positions of electrodes arranged on a head of a wearer according to some example embodiments.

As illustrated in FIG. 3, the electrodes 310 are attached to various positions of the scalp of the wearer, and then an EEG signal is measured when the wearer walks at 2 km per hour, 4 km per hour, and 8 km per hour.

In this case, the positions of the electrodes 310 attached to the scalp of the wearer may follow the International 10-20 system as a general standard, but example embodiments are not limited thereto. Here, the "10" and "20" in 10-20 refer to 10% and 20% inter-electrode distance ratios. For example, the "10" and "20" refer to the fact that the distances between adjacent electrodes are either 10% or 20% of the total front—back or right—left distance of the skull.

As illustrated in FIG. 3, in the international 10-20 system, each site has a letter to identify the lobe and a number to identify the hemisphere location. The letters F, T, C, P and O stand for frontal, temporal, central, parietal, and occipital lobes, respectively. Even numbers (2, 4, 6, 8) refer to electrode positions on the right hemisphere, whereas odd numbers (1, 3, 5, 7) refer to those on the left hemisphere. In addition, the letter codes A, Pg and Fp identify the earlobes, nasopharyngeal and frontal polar sites respectively.

Figure 4:
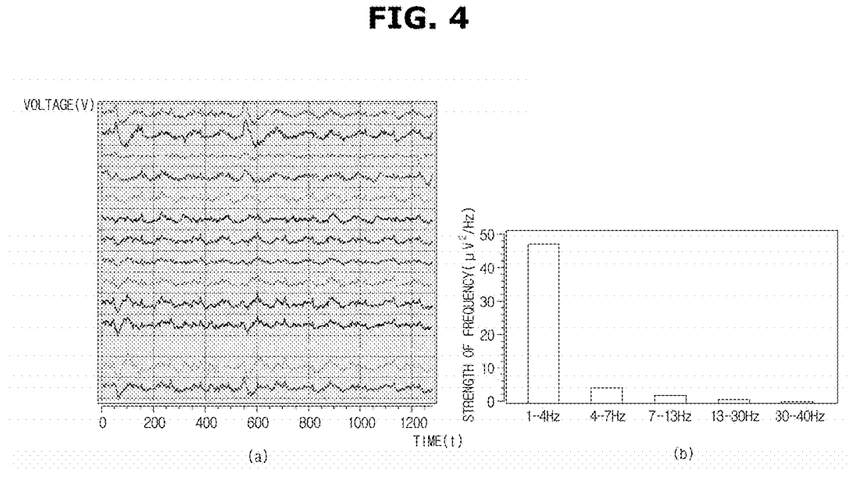
FIG. 4 includes diagrams illustrating an electrical signal measured when a walking speed of the wearer is 2 km per hour and a frequency analysis result.
Figure 5:
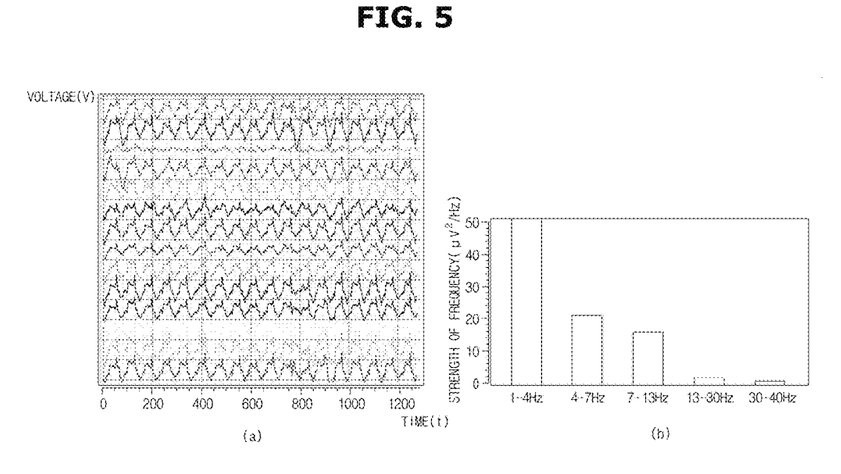
FIG. 5 includes diagrams illustrating an electrical signal measured when a walking speed of the wearer is 4 km per hour and a frequency analysis result.
Figure 6:
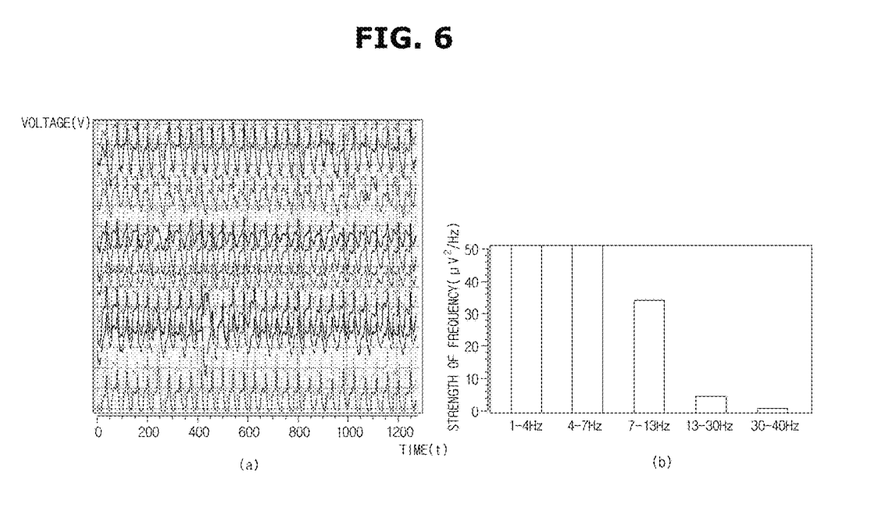
FIG. 6 includes diagrams illustrating an electrical signal measured when a walking speed of the wearer is 8 km per hour and a frequency analysis result.

FIGS. 4 to 6 illustrate a waveform and a frequency analysis result of the third electrical signal that is measured through an electrode AF3 (left frontal lobe) (refer to FIG. 3) when the walking speed of the wearer is 2 km per hour, 4 km per hour, and 8 km per hour, respectively.

As illustrated in FIGS. 4 to 6, as the walking speed increases from 2 km per hour in FIG. 4 to 8 km per hour in FIG. 6, a high frequency component is generated in the waveform of the third electrical signal, and a frequency strength increases in the frequency analysis. The increase in the frequency strength may be due a movement cycle of head muscles becoming faster and an increase in the movement magnitude as the walking speed of the wearer increases.

Figure 7:
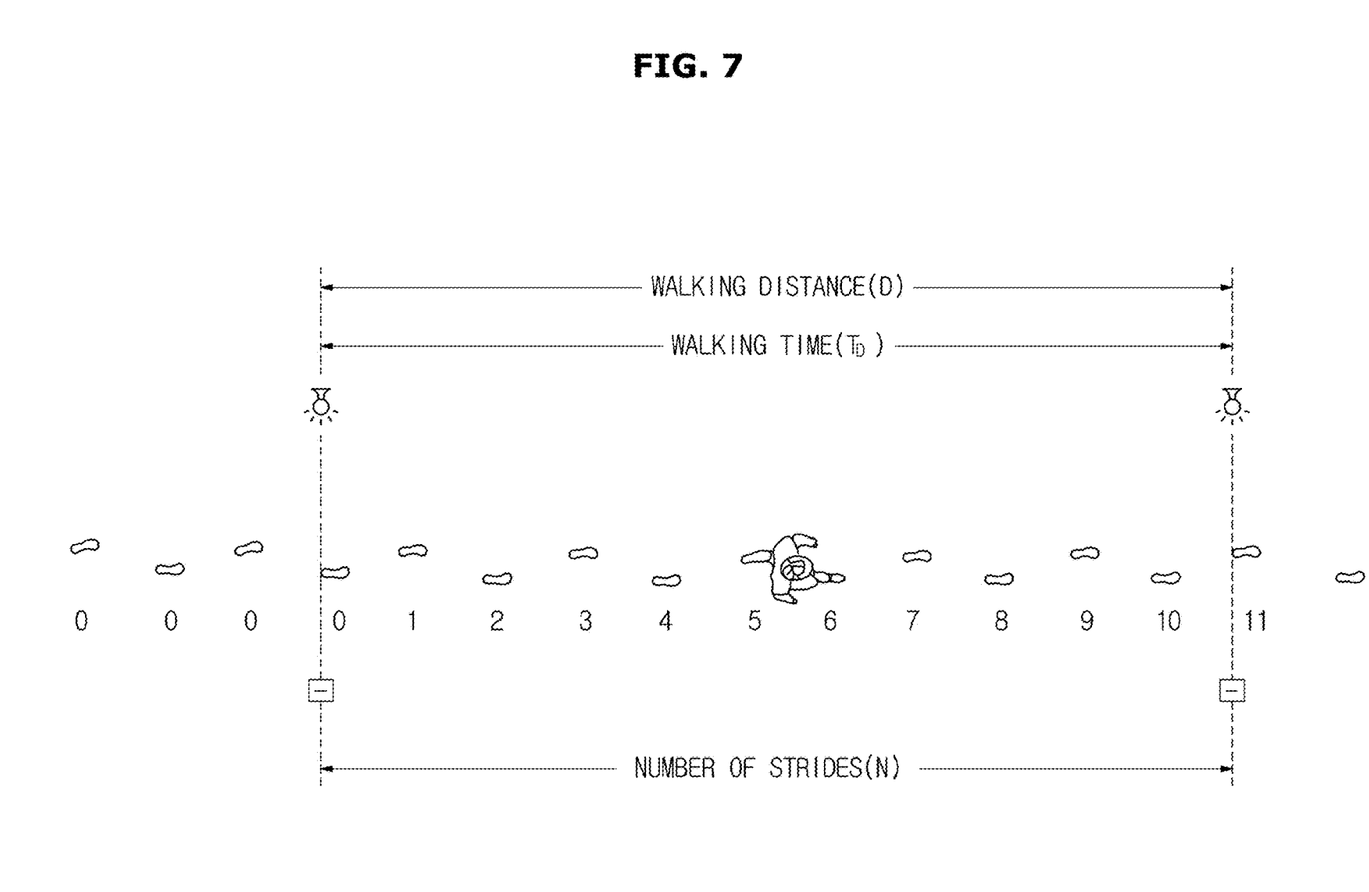
FIG. 7 is a conceptual diagram illustrating a walking distance, a walking time, and the number of strides of the wearer.

FIG. 7 is a conceptual diagram illustrating a walking distance, a walking time, and the number of strides of the wearer.

Referring to FIG. 7, a walking distance (D), a walking time ($T_D$), and the number of strides (N) of the wearer are measured, an average walking speed (V) is obtained by dividing the measured walking distance (D) by the walking time ($T_D$), and a stride cycle (F) may be obtained by dividing the number of strides (N) by the walking time ($T_D$). An average stride length (L) may be obtained by dividing the average walking speed (V) by the stride cycle (F).

Through this experiment, the walking speed and the stride cycle for each average frequency of the third electrical signal of the wearer may be matched and stored in the form of an LUT in the storage unit 400. Therefore, the walking speed estimating unit 220 may estimate a walking speed corresponding to an obtained frequency.

For example, when the frequency analysis is performed on the third electrical signal previously measured for each walking speed and then the obtained average frequency and a corresponding walking speed are matched and stored in the form of an LUT in the storage unit 400, the walking speed estimating unit 220 may calculate the average frequency of the third electrical signal on the actual walk, and find the walking speed corresponding to the calculated average frequency in the LUT stored in the storage unit 400.

In some example embodiments, when the third electrical signal is provided from an electrode, an average value of a frequency of the electrode may be used as the average frequency, and when a plurality of third electrical signals are provided from two or more electrodes, an average value of an average frequency value for each electrode is used as the average frequency.

In this way, the average frequency may be calculated using the following Equation 1.

$$f_{eeg} = \frac{1}{N} \times \sum_{i=1}^{N} f_{ei} \qquad \text{Equation 1}$$

In equation 1, $f_{eeg}$ represents the average frequency of the third electrical signal, N represents the number of electrodes, and $f_{ei}$ represents an average frequency value of an electrode i.

$f_{ei}$ may be calculated using the following Equation 2.

$$f_{ei} = \eta_i \times (F_1 \times P_{1i} + F_2 \times P_{2i} + \ldots + F_m \times P_{mi}) \qquad \text{Equation 2}$$

In Equation 2, $f_{ei}$ represents the average frequency value of the electrode i, $F_1$ represents a first frequency band, $F_2$ represents a second frequency band, $F_m$ represents an mth frequency band, $F_{1i}$ represents a frequency strength of the first frequency band of the electrode i, $P_{2i}$ represents a frequency strength of the second frequency band of the electrode i, and $P_{mi}$ represents a frequency strength of the mth frequency band of the electrode i. In addition, $\eta_i$ may represent a normalizer.

A Second Method of Estimating a Walking Speed

On the other hand, in the second method, a walking speed estimation function obtained based on result data of an experiment that is previously performed is stored in the storage unit 400, the walking speed estimating unit 220 may calculate an average frequency on the actual walk, assign calculated average frequency to the aforementioned walking speed estimation function, and compute a current walking speed estimation value $V_e$.

The walking speed estimation function may be a function in which a stride cycle output function $f(f_{eeg})$ having an average stride length and an average frequency as variables is set as an input and a walking speed is set as an output, but example embodiments are not limited thereto. This walking speed estimation function may be obtained using the following method.

That is, as described above, the stride cycle F for each average frequency of the third electrical signal of the wearer, the walking distance, the walking time, and the number of strides may be measured through the experiment.

The average frequency may be obtained based on a relation between the stride cycle F and the average frequency. The average stride length L may be obtained using the measured walking distance, walking time, and the number of strides. The stride cycle output function $f(f_{eeg})$ may be computed using the average stride length L and the average frequency. Therefore, the walking speed estimation function having the average stride length L and the stride cycle output function $f(f_{eeg})$ as inputs may be obtained.

For example, as illustrated in FIG. 7, the walking distance (D), the walking time ($T_D$), and the number of strides (N) of the wearer are measured, the average walking speed (V) may be obtained by dividing the measured walking distance (D) by the walking time ($T_D$), and the stride cycle (F) may be obtained by dividing the number of strides (N) by the walking time ($T_D$). When the average walking speed (V) obtained in this way is divided by the stride cycle (F), it is possible to obtain the average stride length (L). That is, when the average stride length (L) and the stride cycle (F) are identified, it is possible to obtain the average walking speed (V).

Therefore, the walking speed estimation function in which the stride cycle output function $f(f_{eeg})$ that has the average stride length (L) and the average frequency obtained as described above as variables and outputs the stride cycle (F) is set as an input is obtained. Then, the average frequency of the actually measured third electrical signal is assigned to the stride cycle output function $f(f_{eeg})$. As a result, it is possible to estimate the walking speed. When this walking speed estimation function is represented as a mathematical formula, it is represented as the following Equation 3.

$$V_e = L \times f(f_{eeg})$$ Equation 3

In Equation 3, $V_e$ represents an estimated current walking speed, L represents the average stride length, and $f(f_{eeg})$ represents the stride cycle output function that has the average frequency as a variable and outputs the stride cycle.

In this manner, in some example embodiments, the walking speed estimating unit 220 may estimate the current walking speed of the wearer by assigning the average frequency of the third electrical signal related to walking among the electrical signals measured from the scalp of the wearer to the walking speed estimation function that is obtained through the pre-experiment.

The assistive torque calculating unit 230 may calculate a difference value by comparing the current walking speed of the wearer that is estimated through the aforementioned walking speed estimating unit 220 with a previously input target walking speed, and calculate assistive torque for compensating for the calculated difference value. That is, the assistive torque calculating unit 230 calculates the assistive torque which allows the estimated current walking speed to approximate the target walking speed. A difference value between a current speed and a target speed and assistive torque for compensating for the calculated difference value may be calculated in any known method, therefore, detailed description thereof is omitted.

The mechanical unit 100 may include a mechanism for assisting the wearer with walking, and may include components such as a joint for a walking motion, an actuator such as a motor and hydraulic and pneumatic cylinders, and a belt for attaching to a leg. This mechanical unit 100 may assist the wearer with the walking motion by operations of the joint and the actuator.

As discussed above, with reference to FIG. 1, the mechanical unit 100 may include the waist wearing unit 101, the supporting unit 102, the joint unit 103, the fixing unit 104, and the shoe unit 105, but example embodiments are not limited thereto. Since each configuration has already been described above, description thereof will not be repeated.

As illustrated in FIG. 2, the mechanical unit 100 may include the driving unit 110. The driving unit 110 is configured to deliver driving force for rotation movement to the aforementioned joint 103. In this case, the driving unit 110 may be provided in a number corresponding to the number of joint units 103, but example embodiments are not limited thereto.

Also, although not illustrated in FIG. 2, the wearable robot may further include a mode converting unit (not illustrated).

The mode converting unit may be configured to select a walking mode, a posture mode, a walking speed, and the like. Specifically, the mode converting unit may include a walking mode converting unit (not illustrated) configured to select a walking mode for a flat road, a rough road, stairs, or the like, a posture mode converting unit (not illustrated) configured to select a posture for sitting, standing, a slope, or the like, and/or a walking speed converting unit (not illustrated) configured to select a walking speed such as fast, slow, medium, or the like, but example embodiments are not limited thereto.

The configuration of the wearable robot according to some example embodiments has been described above. In some example embodiments, the wearable robot may measure the electrical signal from the scalp of the wearer using an EEG measurement apparatus for a brain computer interface (BCI), calculate the average frequency by extracting the electrical signal related to walking from among the measured electrical signals, and estimate the current walking speed of the wearer using the calculated average frequency. Accordingly, since the wearable robot according to some example embodiments can measure the walking speed, it may be unnecessary to install a separate apparatus for measuring the walking speed in the mechanical unit.

Hereinafter, a method of controlling a wearable robot will be described.

FIG. 8 is a flowchart sequentially illustrating a method of controlling a wearable robot according to some example embodiments.

As illustrated in FIG. 8, in operation S810, the electrical signal measurement unit 300 may measure the electrical signal from the scalp of the wearer.

For example, the plurality of electrodes 310 of the electrical signal measurement unit 300 may be attached to the scalp of the wearer, and the electrical signal measurement unit 300 may measure the electrical signal from the scalp through the plurality of electrodes 310. The number of electrodes 310 attached to the scalp of the wearer may be one or more.

The electrical signal measured in this operation may include the first electrical signal generated by the electrical activity of the brain of the wearer, the second electrical signal generated by the facial muscle movement, the third electrical signal generated by the head muscle movement upon walking, as well as other electrical signals. In some example embodiments, the electrical signal measurement unit 300 may extract and use only the third electrical signal generated by the head muscle movement upon walking among the electrical signals.

In operation S820, the walking speed estimating unit 220 may estimate the current walking speed of the wearer using the electrical signal measured in operation of S810.

For example, the walking speed estimating unit 220 estimates the current walking speed of the wearer using the third electrical signal among the measured electrical signals, that is, the electrical signal generated by the head muscle movement upon walking. In some example embodiments, to estimate the current walking speed, the walking speed estimating unit 220 may perform the following detailed operations.

First, the third electrical signal is extracted from among the electrical signals measured through the aforementioned operation of S810. The third electrical signal may be extracted from among the various types of electrical signals using various methods.

For example, on some example embodiments, the third electrical signal may be extracted based on a voltage level of the electrical signal may be used. As described above, the electrical signal generated by the electrical activity of the brain may have a value of 100 μV or less, the electrical signal generated by the facial muscle movement may have a value of 10 mV or less, and the electrical signal generated by the head muscle movement upon walking may have a value of 500 μV or less. Therefore, the signal processing unit 220 may extract only the electrical signal having a value in the range of 100 μV to 500 μV from among the measured electrical signals.

Next, the walking speed estimating unit 220 may calculate the average frequency by performing frequency analysis on the extracted third electrical signal. For example, the walking speed estimating unit 220 may analyze the third electrical signal as a plurality of frequency bands, obtain a frequency strength in each frequency band, and then calculate an average frequency value using the obtained frequency strength for each frequency band.

When the third electrical signal is provided from an electrode, the walking speed estimating unit 220 may utilize the average frequency value calculated as described above as the average frequency. When the third electrical signal is provided from two or more electrodes, the walking speed estimating unit 220 may utilize an average value of the calculated average frequency values of all electrodes as a final average frequency. The walking speed estimating unit 220 may calculate the average frequency using the Equations 1 and 2 above.

Next, the walking speed estimating unit 220 may estimate the current walking speed of the wearer based on the calculated average frequency.

The walking speed estimating unit 220 may utilize one or more of at least the following two methods of estimating the current walking speed based on the average frequency, but example embodiments are not limited thereto.

In the first method, an average frequency for each walking speed that is obtained through a pre-experiment is stored in the form of an LUT in the storage unit 400 (refer to FIG. 2), and the walking speed estimating unit 220 may find a walking speed corresponding to the average frequency calculated using the aforementioned method in the LUT stored in the storage unit 400.

On the other hand, in the second method, a walking speed estimation function obtained based on result data of an experiment that is previously performed is stored in the storage unit 400, the walking speed estimating unit 220 may calculate an average frequency on the actual walk, assign the calculated average frequency to the aforementioned walking speed estimation function, and compute a current walking speed estimation value. In this case, since the method of obtaining the walking speed estimation function has already been described above, detailed description thereof will not be repeated.

The walking speed estimation function may be a function in which the stride cycle output function having the average frequency and the stride length of the wearer as variables is set as an input and the walking speed is set as an output. For example, the walking speed estimation function may be represented as the above Equation 3, however, example embodiments are not limited thereto.

Next, in operation S830, the assistive torque calculating unit 230 may calculate a difference value between the current walking speed of the wearer estimated in operation of S820 and the previously input target walking speed. Further, the assistance torque calculating unit 230 may calculate assistive torque for compensating the calculated difference value.

Then, the control unit 200 may generate a control signal for outputting the calculated assistive torque, transmit the generated control signal to the mechanical unit 100. The mechanical unit 100 may output the calculated assistive torque to each joint 103 based on the control signal such that the current walking speed approximates the target walking speed.

Example embodiments have been described above. In the aforementioned example embodiments, some components of the wearable robot may be implemented as a kind of module. Here, the term "module" refers to software or a hardware component such as a field programmable gate array (FPGA) or an application specific integrated circuit (ASIC), and the module can perform certain functions. However, the module is not limited to software or hardware. The module may be configured in a recording medium that can be addressed or may be configured to execute at least one processor.

Examples of the module may include software components, object-oriented software components, class components, components such as task components, processes, functions, properties, procedures, subroutines, segments in program codes, drivers, firmware, microcodes, circuits, data, databases, data structures, tables, arrays, and variables. Components and functions provided from modules may be combined into a smaller number of components and modules or may be further separated into additional components and modules. In addition, the components and modules may execute at least one CPU in a device.

Some example embodiments may be implemented through a medium including a computer readable code or instruction for controlling at least one processing component of the above-described embodiment, for example, a non-transitory computer readable recording medium. The medium may correspond to a medium or media which enable the computer readable code to be stored and/or transmitted.

The computer readable code may be recorded in the medium or transmitted via the Internet. Examples of the medium may include a ROM, a RAM, a CD-ROM, a magnetic tape, a floppy disk, an optical recording medium, and a carrier wave such as data transmission via the Internet. The media may include non-transitory computer readable media. The medium may be a distributed network and thus the computer readable code may be stored, transmitted, or executed in a distributed manner. Moreover, examples of the processing component may include a processor or a computer processor, and the processing component may be distributed and/or included in a single device.

Example embodiments have been described in detail with reference to some of the example embodiments. However, these example embodiments should be considered in a descriptive sense only, and the example embodiments are not limited thereto. It will be apparent to those skilled in the art that various modifications and improvements within the scope of the example embodiments may be made.

Simple modifications and alternations of the example embodiments fall within the scope of the example embodiments and the scope of the example embodiments is defined by the accompanying claims.

What is claimed is:

1. A method of controlling a wearable robot, the wearable robot including sensors and a controller, the method comprising:
    measuring, via the sensors, electrical signals from a scalp of a wearer of the wearable robot such that the measured electrical signals include signals related to at least a head muscle movement of the wearer resulting from the wearer walking;
    estimating, via the controller, a current walking speed of the wearer using the measured electrical signals related to the head muscle movement of the wearer; and
    outputting, via the controller, an assistive torque such that the estimated currant walking speed approximates a target walking speed.

2. The method according to claim 1, wherein the measured electrical signals related to the head muscle movement are a third electrical signal, and the electrical signals further include at least one of:
    a first electrical signal associated with brain activity of the wearer, and
    a second electrical signal associated with facial muscle movement of the wearer.

3. The method according to claim 2, further comprising:
    extracting the third electrical signal from among the measured electrical signals.

4. The method according to claim 3, wherein the extracting the third electrical signal includes determining whether voltage levels of the measured electrical signals are between a lower limit and an upper limit of voltage levels associated with the head muscle movement of the wearer.

5. The method according to claim 3, wherein the estimating a current walking speed of the wearer includes:
    dividing the extracted third electrical signal into a plurality of frequency bands;
    obtaining a frequency strength for each of the frequency bands;
    calculating an average frequency of the third electrical signal using the obtained frequency strength for each frequency band; and
    estimating the current walking speed of the wearer using the calculated average frequency.

6. The method according to claim 5, wherein the estimating the current walking speed of the wearer using the calculated average frequency includes using a lookup table, the lookup table storing therein average frequencies and associated walking speeds.

7. The method according to claim 5, wherein the estimating the current walking speed of the wearer using the average frequency includes assigning the average frequency to a function whose output is the current walking speed, the function having as input variables a stride cycle output function having an average stride length of the wearer and the average frequency.

8. The method according to claim 1, wherein the outputting an assistive torque includes:
    calculating a difference between the current walking speed and the target walking speed;
    determining the assistive torque based on the calculated difference; and
    instructing a driver to drive joints of the wearable robot based on the determined assistance torque.

9. The method according to claim 2, further comprising:
    extracting the third electrical signal from among the measured electrical signals, and wherein
        the estimating the current walking speed includes estimating the current walking speed of the wearer using the extracted third electrical signal, and
    the outputting the assistive torque includes determining the assistive torque based on the estimated current walking speed and the target walking speed.

10. A wearable robot, comprising:
    sensors configured to measure electrical signals from a scalp of a wearer of the wearable robot such that the measured electrical signals include signals related to at least a head muscle movement of the wearer resulting from the wearer walking; and
    a controller configured to,
        estimate a current walking speed of the wearer using the measured electrical signals related to the head muscle movement of the wearer, and
        output an assistive torque such that the estimated current walking speed approximates a target walking speed.

11. The wearable robot according to claim 10, wherein the measured electrical signals related to the head muscle movement are a third electrical signal, and the electrical signals further include at least one of,
    a first electrical signal associated with brain activity of the wearer, and
    a second electrical signal associated with facial muscle movement of the wearer.

12. The wearable robot according to claim 11, wherein the controller includes a processor and a memory, the memory containing computer readable code that, when executed by the processor, configures the processor as:
    a signal processing unit configured to extract the third electrical signal from among the measured electrical signals;
    a walking speed estimating unit configured to estimate the current walking speed of the wearer using the extracted third electrical signal; and
    an assistive torque calculating unit configured to,
        calculate a difference between the estimated current walking speed and the target walking speed,
        determine the assistive torque based on the calculated difference, and
        instruct a driver to drive joints of the wearable robot based on the determined assistance torque.

13. The wearable robot according to claim 12, wherein the signal processing unit is configured to extract the third electrical signal by determining whether voltage levels of the measured electrical signals are between a lower limit and an upper limit of voltage levels associated with the head muscle movement of the wearer.

14. The wearable robot according to claim 12, wherein the walking speed estimating unit is configured to,
- divide the extracted third electrical signal into a plurality of frequency bands,
- obtain a frequency strength for each of the frequency bands,
- calculate an average frequency of the third electrical signal using the obtained frequency strength for each frequency band, and
- estimate the current walking speed of the wearer using the calculated average frequency.

15. The wearable robot according to claim 14, wherein the walking speed estimating unit is configured to estimate the walking speed of the wearer using the calculated average frequency by using a lookup table, the lookup table storing therein average frequencies and associated walking speeds.

16. The wearable robot according to claim 14, wherein the walking speed estimating unit is configured to estimate the walking speed using a walking speed estimation function.

17. The wearable robot according to claim 16, wherein the walking speed estimation function is a function whose output is the current walking speed and input variables are a stride cycle output function having an average stride length of the wearer and the average frequency.

18. The wearable robot according to claim 11, wherein the controller is configured to,
- extract the third electrical signal from among the measured electrical signals,
- estimate the current walking speed of the wearer using the extracted third electrical signal, and
- determine the assistive torque based on the estimated current walking speed and the target walking speed.

\* \* \* \* \*